US00PP10520P

United States Patent [19]

DeLeon

[11] Patent Number: Plant 10,520

[45] Date of Patent: Jul. 21, 1998

[54] AECHMEA PLANT NAMED 'STARBRITE'

[75] Inventor: Nat DeLeon, Goulds, Fla.

[73] Assignee: DeLeon's Bromeliads Inc., Goulds, Fla.

[21] Appl. No.: 797,512

[22] Filed: Feb. 7, 1997

[51] Int. Cl.[6] ..... A01H 5/00

[52] U.S. Cl. ..... Plt./88.8

[58] Field of Search ..... Plt./88.8

*Primary Examiner*—Elizabeth C. Kemmerer

*Attorney, Agent, or Firm*—Burns, Doane, Swecker & Mathis, L.L.P.

[57] ABSTRACT

A new and distinct variety of Aechmea is provided which abundantly forms a large distinctive inflorescence with coral-red bracts and yellow flowers. The foliage of the new variety is dark green and is marked with silver-white coloration. The new variety can be readily distinguished from the 'Friederike' variety (U.S. Plant Pat. No. 5,872) by its blossom coloration, the more openly branched inflorescence, and the degree to which the flower petals emerge from under the floral bracts. Also, the overall inflorescence is cleaner appearing than that of the 'Friederike' variety even with age.

4 Drawing Sheets

SUMMARY OF THE INVENTION

Aechema plants are known to comprise a genus of over 168 species of evergreen perennial suitable for cultivatiion in the home or under glass. Aechmea may be terrestrial or epiphytic. For the most part the plants of the species vary in diameter from 12 to 18 inches to 3 or 4 feet and have rosettes of spiny edged leaves.

The flowers and bracts of Aechmea frequently have brilliant colors and may last up to several months. The range of colors for Aechmea is generally from yellow through orange but may also include pink, orange, red and red-purple. Tubular, three-petaled flowers may also appear but are usually short lived.

Aechmea may be advantageously grown as pot plants for greenhouse or home use. Typically the plants are shaded from direct sunlight and the central vase-like part of the leaf rosette is normally filled with water.

Aechmea is native to tropical America. Leaves of the Aechmea are usually formed as basal rosettes which are stiff and entire and in several vertical ranks. Aechmea have terminal spikes or panicles which are often bracted with the petals united in a tube that is longer than the calyx.

The new variety of Aechmea of the present invention was created during March 1989, at Miami, Fla. by artificial pollination wherein two parents were crossed which previously had been studied in the hope that they would contribute the desired characteristics.

The female parent (i.e., seed parent) was an unnamed *Aechmea tessmannii* selection designated No. 113 (non-patented in the United States), and the male parent (i.e., pollen parent) was an unnamed *Aechmea fasciata* clone designated No. 23 (non-patented in the United States).

The seeds resulting from the above pollination were sown and small plants were obtained which were physically and biologically different from each other. Selective study during July 1992 resulted in the identification of a single plant of the new variety.

It was found that the new variety of the present invention posseses the following combination of characteristics:

(a) forms a large distinctive inflorescence having coral-red bracts and yellow flowers, and (b) forms attractive dark green foliage that is marked with a silver-white coloration.

The new variety of the present invention can be readily distinguished from Aechmea 'Friederike' (U.S. Plant Pat. No. 5,872). More specifically, the new variety forms bright coral-red bracts while those of the 'Friederike' variety are vermillion red, the inflorescence is more optically branched and generally is displayed longer than that of the 'Friederike' variety, the flower petals are yellow while those of the 'Friederike' variety are blue, the flower petals emerge only slightly from under the floral bracts while those of the 'Friederike' variety tend to more completely emerge, and the leaves are considerably wider than those of the 'Friederike' variety. It is found that the inflorescence of the new variety overall is considerably cleaner appearing than that of the 'Friederike' variety even with age. Also, on the new variety the spent flowers are barely visible, while those of the 'Freiderike' variety turn black-brown when spent and tend to persist on the plant as long as the floral bracts display color.

The new variety has been carefully evaluated and has been found to undergo asexual propagation at Goulds, Fla. beginning in December, 1992. More specifically, asexual propagation by the cutting of off-shown growing from the base of the plant has shown that the characteristics of the new variety are stable and are strictly transmissible from one generation to another.

The new variety of the present invention has been named the 'Starbrite' variety.

The new 'Starbrite' variety has not been observed and tested under all possible environmental conditions to date. Accordingly, the phenotype may vary with variations in environmental conditions, such as temperature, light intensity, day length, humidity, etc., without any change in the genotype.

BRIEF DESCRIPTION OF THE PHOTOGRAPH

The accompanying photographs show as nearly true as it is reasonably possible to make the same in color illustrations of this character typical specimens of the plant and the foliage of the new variety. The plant was grown in a greenhouse at Goulds, Fla., while using growing conditions that are standard for the industry.

FIG. 1 illustrates the original plant of the new variety after 21 months of growth when finished in a 20 cm. pot. The abundant branching propensity of the new variety is shown.

FIG. 2 illustrates a closer view of the inflorescence of the new variety. The attractive bright coral-red bracts and the separation of the branches are shown.

FIG. 3 illustrates a very close view of the inforescence of the new variety. The flowering habit and the yellow flowers that commonly extend only slightly beyond the floral bracts are shown.

FIG. 4 illustrates the spineless nature of the leaves of the new variety.

DETAILED DESCRIPTION

The chart used in the identification of colors is that of The Royal Horticulturual Society (R.H.S. Colour Chart). The description is based upon the observation of the plant of FIG. 1 when grown at Goulds, Fla. under greenhouse conditions that are standard for the industry.

Classification: *Aechmea tessmannii*×*Aechmea fasciata*. cv. 'Starbrite'.

Plant:

*Growth habit.*—Basal rosettes of laxly spreading strap-like leaves arranged around a central axis.

*Height.*—Approximately 50 to 80 cm. including inflorescence.

*Diameter.*—Approximately 50 to 70 cm.

Foliage:

*Leaf size.*—The basal leaves are approximately 38 to 68 cm. in length, and approximately 6 to 12 cm. in width.

*Leaf shape.*—The leaf blade is ligulate with a broadly acute to rounded apiculate apex, slightly channeled, and the margins are entire and spineless.

*Leaf sheath.*—Elliptic, approximately 12 to 18 cm. in length, and approximately 8 to 12 cm. in width.

*Leaf texture.*—The leaf blade is thick, coriaceous, and with scattered silver-white trichomes. The silver-white lepidote is dense on the abaxial surface of the leaves.

*Leaf color.*—The adaxial surface is green group 137A marked with silver-white trichomes of greyed-green group 191A. The abaxial surface is greyer than green group 137A with dense silver-white lepidote of greyed-green group 191A.

*Number of leaves.*—The plant commonly produces approximately 16 to 28 leaves before producing an inflorescence.

*Roots.*—Wiry with fine laterals, and yellow-green changing to brown in coloration.

Bracts:

*Primary bracts.*—The primary bracts number approximately 18 to 25, are thin, possess a surface that sparsely bears white lepidote particularly on the abaxial surface, possess a margin that is entire or irregularly or laxly serrate, and are located at the base of each branch spike. The length is approximately 6.5 to 12.5 cm. and the width is approximately 1.2 to 2.8 cm., and the shape is lanceolate with acute to acuminate tips which terminate in a sharp point. The adaxial and abaxial surfaces are near red group 43A in coloration.

*Floral bracts.*—The floral bracts underlying the flowers are elliptic with acute to acuminate tips which terminate in a sharp point which recurves slightly, moderately thick, proximal carinate, distal ecarinate, possess a distal surface that is glabrous, and a proximal surface that is sparce lepidote, commonly number approximately 450 and are approximately 2.5 to 3.5 cm. in length and approximately 1.2 to 1.5 cm. in width. The adaxial surface is near red group 43C in coloration.

*Scape bracts.*—The scape bracts are thin with scattered white trichomes, upright, overlapping and encircle the scape, possess a margin that is irregularly and laxly serrate, number approximately 10, are approximately 6 to 7.5 cm. in length and approximately 2.5 cm. in width, and possess a shape that is lanceolate with an acuminate recurving tip. The adaxial and abaxial surfaces are near red group 43D in coloration.

*Scape.*—the surface is densely covered with white floccose trichomes, the height is approximately 40 to 50 cm., the diameter is approximately 1.5 to 2.4 cm., and the color is mostly obscurred.

*Branch spikes.*—The branches are positioned at about 45° to 60° with respect to the main axis. The branches commonly are approximately 8 to 12 cm. in length, and approximately 2 to 3 cm. in width and approximately 18 to 25 branch spikes commonly are present. Approximately 15 to 25 buds/flowers commonly are present on each branch spike.

*Shape of Inflorescence.*—Bi-pennate or tri-pennate, commonly approximately 24 to 28 cm. in height, and commonly approximately 18 to 24 cm. in width.

Flowers:

*Calyx.*—Three oblong sepals are present, approximately 15 mm. in length, and yellow group 8C tinged with orange group 29C in coloration.

*Corolla.*—Tubular, three ligulate petals are present, approximately 22 to 24 mm. in length, with each a pair of appendages approximately 22 to 24 mm. above the base, and yellow group 11B in coloration.

*The flowering of mature plants commonly begins approximately* 10 to 12 weeks after induction during the warm summer months, and approximately

*Time of blooming.*—12 to 15 weeks after induction during the cool winter months.

*Duration of inflorescence.*—The inflorescence commonly will hold its color approximately 4 to 6 months depending upon cultural conditions and the season of the year.

Floral organs:

*Ovary.*—Broadly ellipsoid, trigonous, approximately 8 to 9 mm. in length, approximately 7 to 8 mm. in width, and pale yellow-green group 154D in coloration.

*Anthers.*—Approximately 5 mm. in length, and apparently nonfunctional.

Seed characteristics: Appears to be a sterile $F_1$ hybrid.

I claim:

1. A new and distinct variety of Aechmea plant characteristics by the following combination of characteristics:

(a) forms a large distinctive inflorescence having coral-red bracts and yellow flowers, and (b) forms attractive dark green foliage that is marked with silver-white coloration;

substantially as herein illustrated and described.

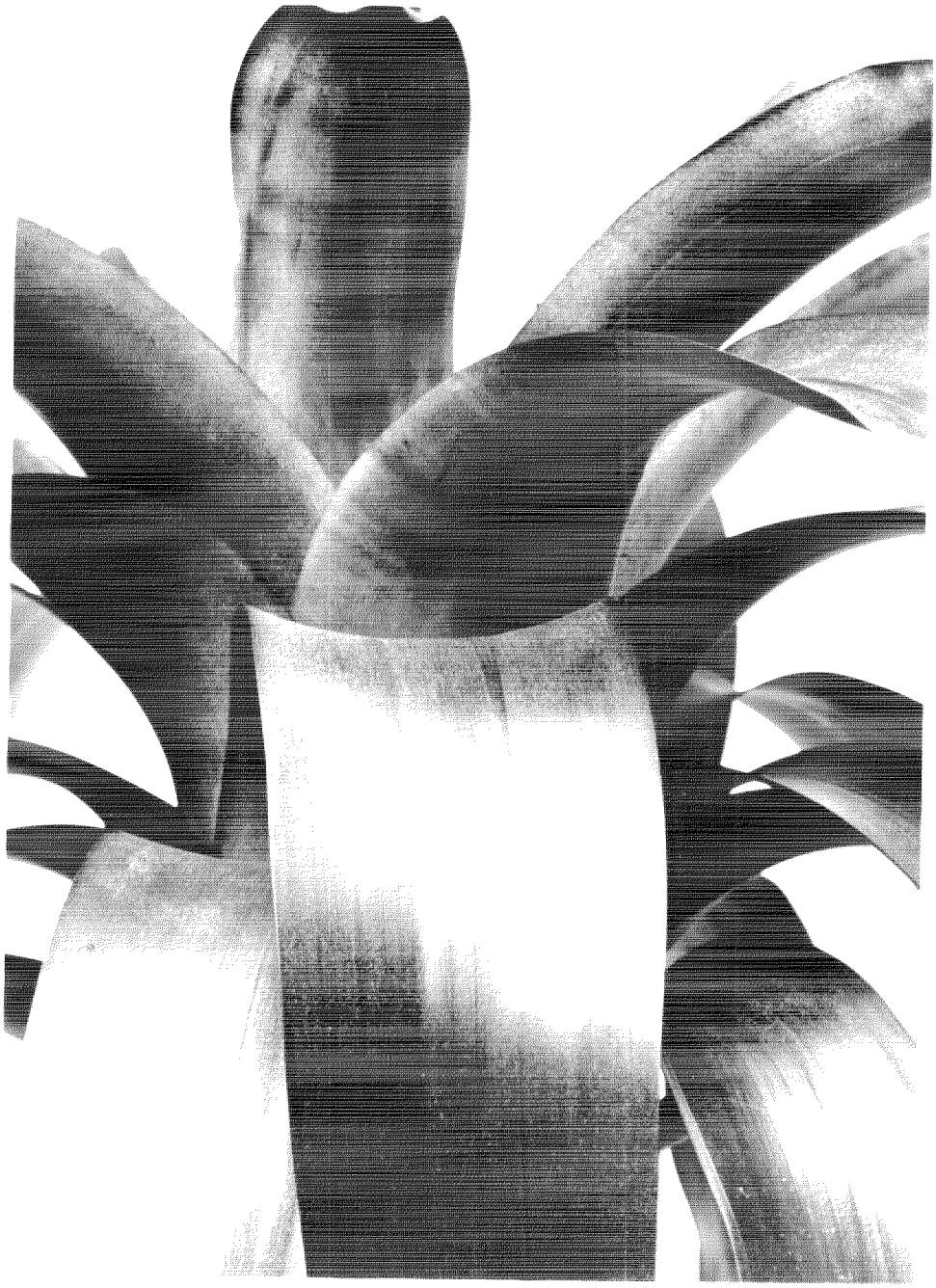

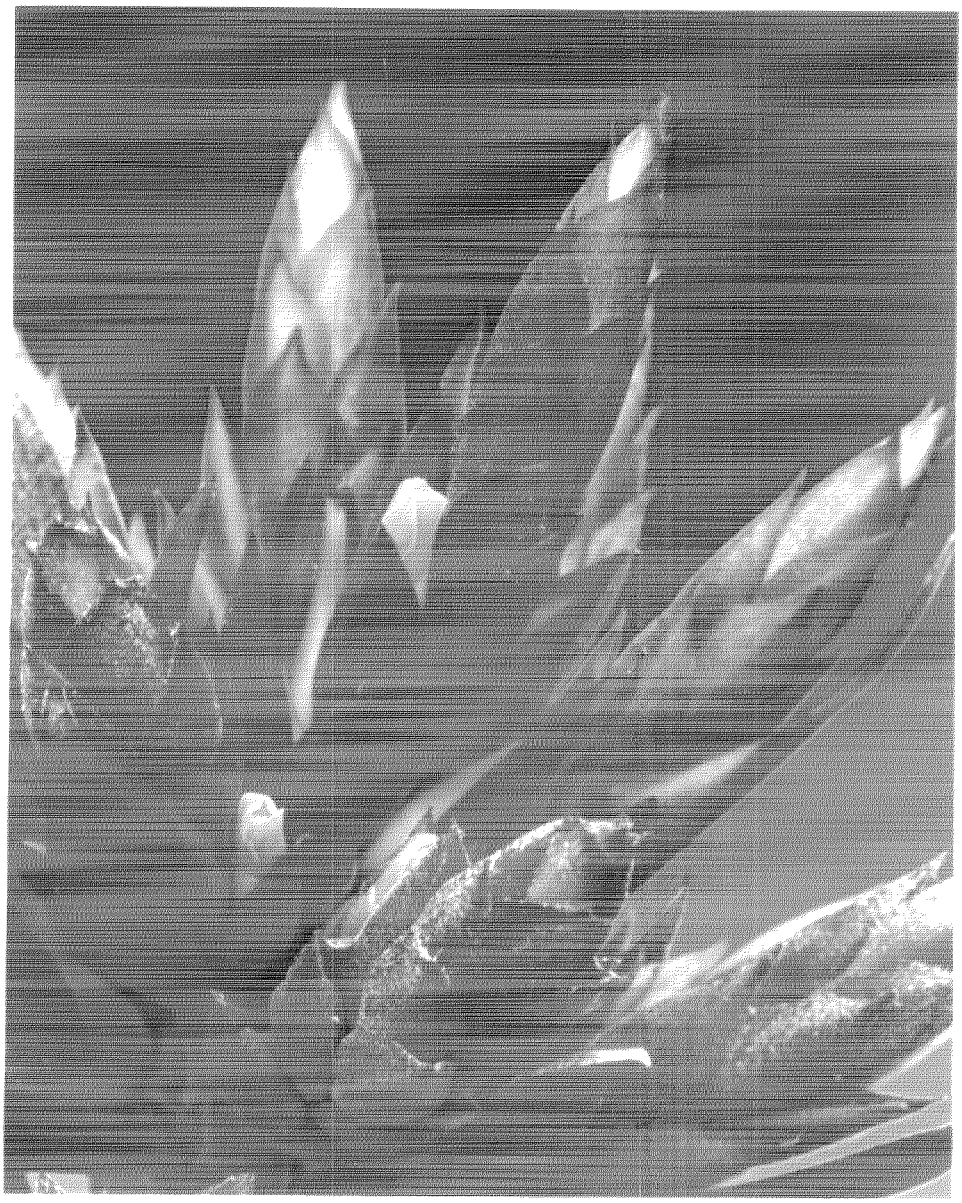

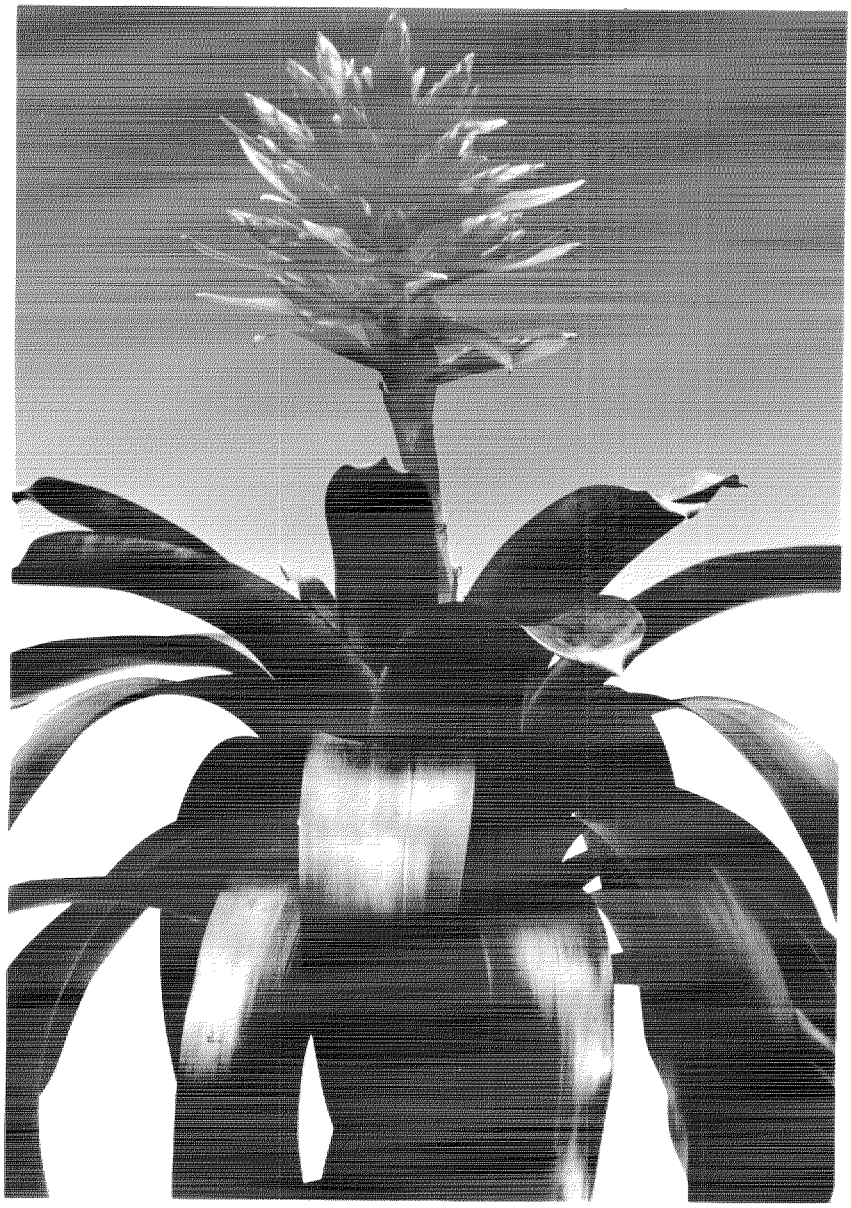

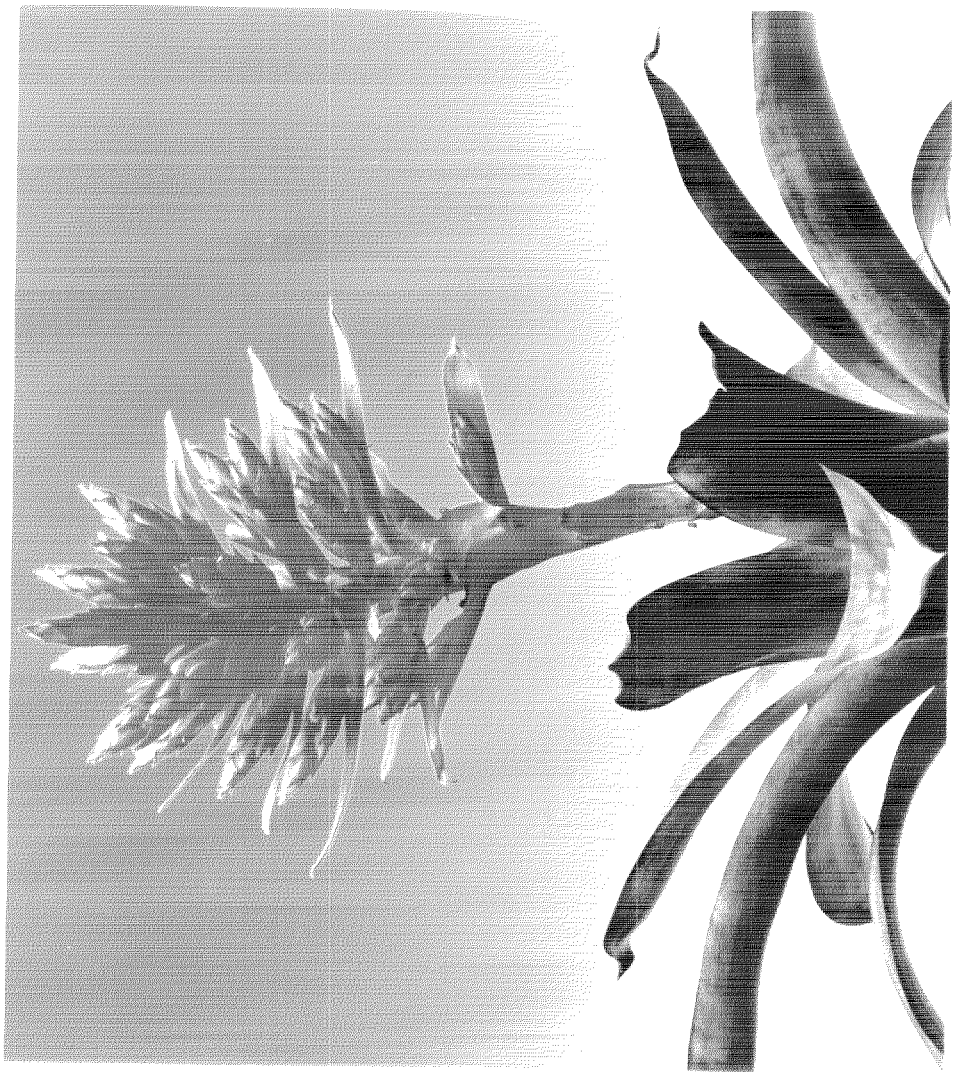

* * * * *